United States Patent
Fliri et al.

(10) Patent No.: US 7,196,161 B2
(45) Date of Patent: Mar. 27, 2007

(54) 3-ETHER AND 3-THIOETHER SUBSTITUTED CYCLOSPORIN DERIVATIVES FOR THE TREATMENT AND PREVENTION OF HEPATITIS C INFECTION

(75) Inventors: Hans Georg Fliri, Walden (GB); David Renwick Houck, Cary, NC (US)

(73) Assignee: Scynexis Inc., Research Triangle Park, NC (US)

( * ) Notice: Subject to any disclaimer, the term of this patent is extended or adjusted under 35 U.S.C. 154(b) by 0 days.

(21) Appl. No.: 11/241,650

(22) Filed: Sep. 30, 2005

(65) Prior Publication Data

US 2006/0089301 A1 Apr. 27, 2006

Related U.S. Application Data

(60) Provisional application No. 60/707,626, filed on Aug. 11, 2005, provisional application No. 60/615,152, filed on Oct. 1, 2004.

(51) Int. Cl.
*C07K 7/64* (2006.01)
(52) U.S. Cl. ......................... 530/317; 514/11
(58) Field of Classification Search ................ 530/317; 514/11
See application file for complete search history.

(56) References Cited

U.S. PATENT DOCUMENTS

| | | | |
|---|---|---|---|
| 4,703,033 A | 10/1987 | Seebach | |
| 4,771,122 A | 9/1988 | Seebach | |
| 4,798,823 A | 1/1989 | Witzel | |
| 4,814,323 A | 3/1989 | Andrieu et al. | |
| 4,885,276 A | 12/1989 | Witzel | |
| 4,996,193 A | 2/1991 | Hewitt et al. | |
| 5,294,604 A | 3/1994 | Nussenblatt | |
| 5,948,755 A | 9/1999 | Barriere et al. | |
| 5,948,884 A | 9/1999 | Luchinger | |
| 5,965,527 A | 10/1999 | Barriere et al. | |
| 5,977,067 A | 11/1999 | Evers et al. | |
| 5,981,479 A | 11/1999 | Ko et al. | |
| 5,994,299 A | 11/1999 | Barriere et al. | |
| 6,254,860 B1 | 7/2001 | Garst | |
| 6,350,442 B2 | 2/2002 | Garst | |
| 6,444,643 B1 | 9/2002 | Steiner et al. | |
| 6,521,595 B1 | 2/2003 | Kim et al. | |
| 6,583,265 B1 | 6/2003 | Ellmerer-Muller et al. | |

FOREIGN PATENT DOCUMENTS

| | | |
|---|---|---|
| WO | WO98/28328 | 7/1998 |
| WO | WO98/28329 | 7/1998 |
| WO | WO98/28330 | 7/1998 |
| WO | WO0001715 | 1/2000 |
| WO | WO2005/021028 | 3/2005 |
| WO | WO2006/005610 | 1/2006 |
| WO | WO06038088 | 4/2006 |

OTHER PUBLICATIONS

Hansson et al., 2004, "The Nonimmunosuppressive Cyclosporin Analogs NIM811 and UNIL025 Display Nanomolar Potencies on Permeability Transition in Brain Derived Mitochondria," *Journal of Bioenergetics and Biomembranes*, 36(4):407-413.

Hubler et al., 2000, "Synthetic Routes to NEtXaa[4]-Cyclosporin A Derivatives as Potential Anti-HIV I Drugs," *Tetrahedron Letters* 41(37):7193-7196.

Inoue et al., 2005, "Interferon Combined with Cyclosporin Treatment as an Effective Countermeasure Against Hepatitis C Virus Recurrence in Liver Transplant Patients with End-Stage Hepatitis C Virus Related Disease," *Transplantation Proceedings*. 37(2):1233-1234.

Xia et al., 2005, "Inhibitory Effect of Cyclosporine A on Hepatitis B Virus Replication *in Vitro* and its Possible Mechanisms," *Hepatobiliary &Pancreatic Diseases International*, 4(1):18-22.

DebioPharm Press Release, New Data Presented on Debiopharm's Debio-25 at the 11th International Symposium on the Hepatitis C Virus and Related Viruses in Heidelberg, Germany, Oct. 6, 2004.

Nakagawa et al., 2004, "Specific inhibition of hepatitis C virus replication by cyclosporin A," *Biochem. Biophys. Res. Commun.* 313:42-7.

Watashi et al., 2003, "Cyclosporin A suppresses replication of hepatitis C virus genome in cultured hepatocytes," *Hepatology* 38:1282-1288.

Shimotohno and Watashi, 2004, *American Transplant Congress*, Abstract No. 648 (American Journal of Transplantation, 2004, 4(s8):1-653).

*Primary Examiner*—David Lukton
(74) *Attorney, Agent, or Firm*—Jones Day

(57) ABSTRACT

This invention relates to cyclosporin derivatives of general formula (I):

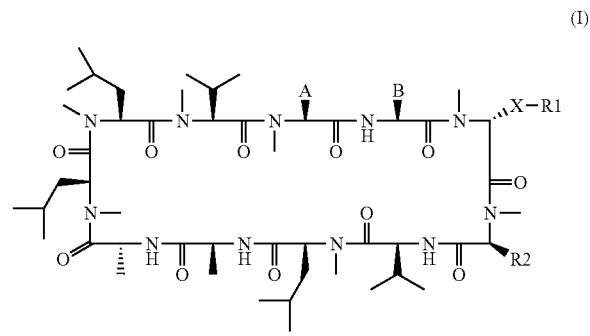

wherein A, B, $R^1$, $R^2$ and X are as defined in the specification, and pharmaceutical compositions prepared from the same, for use in treatment of hepatitis C virus.

11 Claims, No Drawings

3-ETHER AND 3-THIOETHER SUBSTITUTED CYCLOSPORIN DERIVATIVES FOR THE TREATMENT AND PREVENTION OF HEPATITIS C INFECTION

The instant application claims the benefit under 35 U.S.C. §119 of U.S. Provisional Application Nos. 60/615,152, filed Oct. 1, 2004, and 60/707,626, filed Aug. 11, 2005, the contents of which are hereby incorporated by reference in their entireties.

1. FIELD OF THE INVENTION

The present invention provides cyclosporin derivatives and pharmaceutical compositions prepared from the same, for use in treatment or prevention of hepatitis C virus infection in a subject in need thereof. In certain aspects, the present invention provides methods of treating hepatitis C infection by administering to a subject in need thereof an amount of a 3-ether or 3-thioether cyclosporin of the invention effective to treat or prevent the infection.

2. BACKGROUND

In 1989, a main causative virus of non-A non-B post-transfusion hepatitis was found and named hepatitis C virus (HCV). Since then, several types of hepatitis viruses have been found besides type A, type B and type C, wherein hepatitis caused by HCV is called hepatitis C. Subjects infected with HCV are considered to involve several percent of the world population, and infection with HCV characteristically becomes chronic.

HCV is an envelope RNA virus, wherein the genome is a single strand plus-strand RNA, and belongs to the genus Hepacivirus of Flavivirus (from The International Committee on Taxonomy of Viruses, International Union of Microbiological Societies). Of the same hepatitis viruses, for example, hepatitis B virus (HBV), which is a DNA virus, is eliminated by the immune system, and infection with this virus ends in an acute infection except for neonates and infants having yet immature immunological competence. In contrast, HCV somehow avoids the immune system of the host due to an unknown mechanism. Once infected with this virus, even an adult having a mature immune system frequently develops persistent infection.

When chronic hepatitis is associated with the persistent infection with HCV, it advances to cirrhosis or hepatic cancer in a high rate. Enucleation of tumor by operation does not help much, because the subject often develops recurrent hepatic cancer due to the sequela inflammation in non-cancerous parts.

Thus, an effective therapeutic method for treating hepatitis C infection is desired. Apart from the symptomatic therapy to suppress inflammation with an anti-inflammatory agent, the development of a therapeutic agent that reduces HCV to a low level free from inflammation and that eradicates HCV has been strongly demanded. An optimal therapeutic agent would provide a virologic response classified as a "sustained virologic response," which is defined as undetectable levels of virus in blood six months or more after completing hepatitis C therapy.

At present, treatments with interferon, as a single agent or in combination with ribavirin, are the only effective method known for the eradication of HCV. However, interferon can eradicate the virus only in about 33–46% of the subject population. For the rest of the subjects, it has no effect or provides only a temporary effect. Therefore, an anti-HCV drug to be used in the place of or concurrently with interferon is awaited in great expectation.

Cyclosporin A is well known for its immunosuppressive activity and a range of therapeutic uses, including antifungal, anti-parasitic, and anti-inflammatory as well as anti-HIV activity. Cyclosporin A and certain derivatives have been reported as having anti-HCV activity, see Watashi et al., 2003, *Hepatology* 38:1282–1288, Nakagawa et al., 2004, *Biochem. Biophys. Res. Commun.* 313:42–7, and Shimotohno and Watashi, 2004, *American Transplant Congress*, Abstract No. 648 (American Journal of Transplantation, 2004, 4(s8): 1–653).

However, a problem with known cyclosporins is their nephrotoxicity. For example, cyclosporin A (cyclosporine) can cause nephrotoxicity and hepatotoxicity. Nephrotoxicity, a serious complication of cyclosporine therapy, is characterized by intense renal vasoconstriction that often progresses to chronic injury with irreversible structural renal damage (Busauschina et al., 2004; Myers et al., 1988). Nephrotoxicity associated with cyclosporine has been noted in 25 to 38% of transplant subjects. Renal dysfunction can occur at any time and ranges from an early reversible damage to a late progression to irreversible chronic renal failure. Acute nephrotoxicity may appear soon after transplantation or after weeks or months, with oliguria, acute decrement of glomerular filtration rate and renal plasma flow (Kahan, 1989).

In prolonged cyclosporine administration, chronic nephrotoxicity is characterized by a progressive and mostly irreversible impairment of renal function, and it is supported by histological lesions ranging from striped fibrosis to ischemic collapse of the tuft, glomerular sclerosis and tubular atrophy.

Effective methods and compositions for the treatment or prevention of hepatitis C infection are needed to combat the virus worldwide.

3. SUMMARY OF THE INVENTION

Surprisingly it has found that certain 3-substituted cyclosporin derivatives have activity against HCV. Also, it has been found that certain of said 3-substituted cyclosporin derivatives have unexpectedly good toxicological profiles.

In one aspect the present invention provides cyclosporin derivatives having activity against HCV. In certain embodiments, the present invention provides methods of treating or preventing hepatitis C infection in a subject in need thereof by administering to the subject an effective amount of a 3-substituted cyclosporin derivative of the invention. In certain embodiments, the 3-substituted cyclosporin derivative is selected from the group consisting of a 3-ether cyclosporin; a 3-ether, 4-gamma-hydroxymethylleucine cyclosporin; a 3-thioether cyclosporin; and a 3-thioether, 4-gamma-hydroxymethylleucine cyclosporin.

In a further aspect the present invention provides cyclosporin derivatives having activity against HCV with an improved safety margin (i.e. the difference between the dose level of compound required to provide effective control of HCV and the dose levels producing toxicity).

In a further aspect the present invention provides cyclosporin derivatives having improved nephrotoxicity and/or hepatotoxicity in comparison with known compounds.

In another aspect, the present invention provides a method for treating or preventing hepatitis C virus infection in a subject. In certain aspects, the method of the invention comprises administering, to a subject in need thereof, an effective amount of a cyclosporin compound with a high therapeutic index against hepatitis C virus. The therapeutic index, or the ratio of cytotoxic concentration to viral inhibitory concentration, is described in detail below.

In another aspect, the present invention provides a method comprising administering a therapeutically effective amount of a cyclosporin derivative of general formula (I):

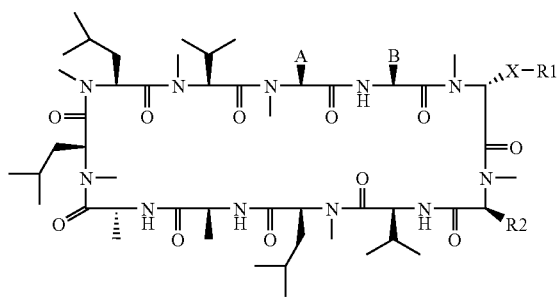

(I)

wherein:

A is residue of formula (IIa) or (IIb):

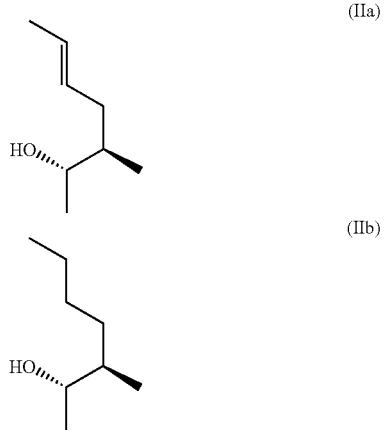

(IIa)

(IIb)

B is ethyl, 1-hydroxyethyl, isopropyl or n-propyl;

$R^1$ represents:
straight- or branched-chain alkyl containing from one to six carbon atoms, optionally substituted by one or more groups $R^3$ which may be the same or different;
straight- or branched-chain alkenyl containing from two to six carbon atoms optionally substituted by one or more groups which may be the same or different selected from the group consisting of halogen, hydroxy, amino, monoalkylamino and dialkylamino;
straight- or branched-chain alkynyl containing from two to six carbon atoms, optionally substituted by one or one or more groups which may be the same or different selected from the group consisting of halogen, hydroxy, amino, monoalkylamino and dialkylamino;
cycloalkyl containing from three to six carbon atoms optionally substituted by one or more groups which may be the same or different selected from the group consisting of halogen, hydroxy, amino, monoalkylamino and dialkylamino;
straight- or branched-chain alkoxycarbonyl containing from one to six carbon atoms;

$R^2$ represents isobutyl or 2-hydroxyisobutyl;
X represents —S(O)$_n$— or oxygen;
$R^3$ is selected from the group consisting of halogen, hydroxy, carboxyl, alkoxycarbonyl, —NR$^4$R$^5$ and —NR$^6$(CH$_2$)$_m$NR$^4$R$^5$;
$R^4$ and $R^5$, which may be the same or different, represent:
hydrogen;
straight- or branched-chain alkyl comprising from one to six carbon atoms, optionally substituted by one or more groups $R^7$ which may be the same or different;
straight- or branched-chain alkenyl or alkynyl comprising from two to four carbon atoms;
cycloalkyl containing from three to six carbon atoms optionally substituted by straight- or branched-chain alkyl containing from one to six carbon atoms;
phenyl optionally substituted by from one to five groups which may be the same or different selected from the group consisting of halogen, alkoxy, alkoxycarbonyl, amino, alkylamino and dialkylamino;
a heterocyclic ring which may be saturated or unsaturated containing five or six ring atoms and from one to three heteroatoms which may the same or different selected from nitrogen, sulfur and oxygen;
or $R^4$ and $R^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four groups which may be the same or different selected from the group consisting of alkyl, phenyl and benzyl;
$R^6$ represents hydrogen or straight- or branched-chain alkyl containing from one to six carbon atoms;
$R^7$ is selected from the group consisting of halogen, hydroxy, carboxyl, alkoxycarbonyl and —NR$^8$R$^9$;
$R^8$ and $R^9$ which may be the same or different, each represent hydrogen or straight- or branched-chain alkyl containing from one to six carbon atoms;
n is zero, one or two;
m is an integer from two to four;
halogen means fluoro, chloro, bromo or iodo;
or a pharmaceutically acceptable salt thereof.

In certain embodiments, X is O. In other embodiments X is S.

In certain cases the substituents A, B, $R^1$ and $R^2$ may contribute to optical and/or stereoisomerism. All such forms are embraced by the present invention.

Mention may be made, as examples of pharmaceutically acceptable salts, of the salts with alkali metals, e.g., sodium, potassium or lithium, or with alkaline-earth metals, e.g., magnesium or calcium, the ammonium salt or the salts of nitrogenous bases, e.g., ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine.

Mention may be made, as examples of addition salts with pharmaceutically acceptable acids, of the salts formed with inorganic acids, e.g., hydrochlorides, hydrobromides, sulfates, nitrates or phosphates, or with organic acids, e.g., succinates, fumarates, tartrates, acetates, propionates, maleates, citrates, methanesulfonates, ethanesulfonates, p-toluenesulfonates, isethionates or embonates, or with substitution derivatives of these compounds. Preferred salts are succinate, phosphate, citrate, acetate, hydrochlorides, methanesulfonate and propionate. Certain of these salts are novel and as such constitute a further feature of the present invention.

Accordingly, in certain aspects, the present invention provides novel salts of the compounds described herein. In certain embodiments, the present invention provides a salt of a compound according to formula I, wherein the salt is selected from the group consisting of hydrochlorides, hydrobromides, sulfates, nitrates, phosphates, succinates, fumarates, tartrates, acetates, propionates, maleates, citrates, methanesulfonates, ethanesulfonates, p-toluenesulfonates, isethionates and embonates. In certain embodiments, the salt is selected from the group consisting of succinate, phosphate, citrate, acetate, hydrochloride, methanesulfonate and propionate.

4. DESCRIPTION OF PREFERRED EMBODIMENTS

The present invention provides methods of treating or preventing hepatitis C infection in a subject in need thereof, and pharmaceutical compositions and dosage forms useful for such methods. The methods and compositions are described in detail in the sections below.

4.1 Definitions

When referring to the compounds and complexes of the invention, the following terms have the following meanings unless indicated otherwise.

"Cyclosporin" refers to any cyclosporin compound known to those of skill in the art, or a derivative thereof. See, e.g., Ruegger et al., 1976, *Helv. Chim. Acta.* 59:1075–92; Borel et al., 1977, *Immunology* 32:1017–25; the contents of which are hereby incorporated by reference in their entireties. Exemplary compounds of the invention are cyclosporin derivatives. Unless noted otherwise, a cyclosporin described herein is a cyclosporin A, and a cyclosporin derivative described herein is a derivative of cyclosporin A.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Alkyl" refers to monovalent saturated aliphatic hydrocarbyl groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms.

"Alkylene" refers to divalent saturated aliphatic hydrocarbyl groups particularly having up to about 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenyl" refers to monovalent olefinically unsaturated hydrocarbyl groups preferably having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkynyl" refers to acetylenically unsaturated hydrocarbyl groups particularly having up to about 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkylamino" refers to the group alkyl-NR'—, wherein R' is selected from hydrogen and alkyl.

"Arylamino" refers to the group aryl-NR'—, wherein R' is selected from hydrogen, aryl and heteroaryl.

"Alkoxycarbonyl" refers to a radical —C(O)-alkoxy where alkoxy is as defined herein.

"Amino" refers to the radical —NH2.

"Carboxy" refers to the radical —C(O)OH.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Halogen" or "halo" refers to chloro, bromo, fluoro or iodo.

"Hydroxy" refers to the radical —OH.

"Nitro" refers to the radical —NO$_2$.

"Thioalkoxy" refers to the group —SR where R is alkyl.

"Sulfanyl" refers to the radical HS—. "Substituted sulfanyl" refers to a radical such as RS— wherein R is any substituent described herein. In certain embodiments, "substituted sulfanyl" refers to a radical —SR where R is an alkyl or cycloalkyl group as defined herein that may be optionally substituted as defined herein. Representative examples include, but are not limited to, methylthio, ethylthio, propylthio, butylthio, and the like.

"Sulfinyl" refers to the radical —S(O)H. "Substituted sulfinyl" refers to a radical such as S(O)—R wherein R is any substituent described herein.

"Sulfonyl" refers to the divalent radical —S(O$_2$)—. "Substituted sulfonyl" refers to a radical such as —S(O$_2$)—R wherein R is any substituent described herein. In particular embodiments, R is selected from H, lower alkyl, alkyl, aryl and heteroaryl.

"Pharmaceutically acceptable salt" refers to any salt of a compound of this invention which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound of the present invention or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413–447, *Angew. Chem., Int. Ed. Engl.* 5:385–414 (errata: *Angew. Chem., Int. Ed. Engl.* 5:511); Prelog and Helmchen, 1982, *Angew. Chem.* 94:614–631, *Angew. Chem. Internat. Ed. Eng.* 21:567–583; Mata and Lobo, 1993, *Tetrahedron: Asymmetry* 4:657–668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture."

In certain embodiments, the compounds of this invention may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon treatment with base.

In certain embodiments, the compounds of the invention are "stereochemically pure." A stereochemically pure compound or has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

"Sarcosine" or "Sar" refers to the amino acid residue known to those of skill in the art having the structure —N(Me)CH$_2$C(O)—. Those of skill in the art might recognize sarcosine as N-methyl glycine.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a monkey such as a cynomolgous monkey, a chimpanzee and a human), and more preferably a human. In one embodiment, the subject is refractory or non-responsive to current treatments for hepatitis C infection. In another embodiment, the subject is a farm animal (e.g., a horse, a cow, a pig, etc.) or a pet (e.g., a dog or a cat). In a preferred embodiment, the subject is a human.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound of the invention. In certain other embodiments, the term "therapeutic agent" refers does not refer to a compound of the invention. Preferably, a therapeutic agent is an agent which is known to be useful for, or has been or is currently being used for the treatment, management, prevention, or amelioration of a disorder or one or more symptoms thereof.

"Therapeutically effective amount" means an amount of a compound or complex or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in one embodiment, to ameliorating a disease or disorder that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound of the invention. In certain other embodiments, the term "prophylactic agent" does not refer a compound of the invention. Preferably, a prophylactic agent is an agent which is known to be useful for, or has been or is currently being used to the prevent or impede the onset, development, progression and/or severity of a disorder.

As used herein, the terms "prevent," "preventing" and "prevention" refer to the prevention of the recurrence, onset, or development of one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the phrase "prophylactically effective amount" refers to the amount of a therapy (e.g., prophylactic agent) which is sufficient to result in the prevention of the development, recurrence or onset of one or more symptoms associated with a disorder (, or to enhance or improve the prophylactic effect(s) of another therapy (e.g., another prophylactic agent).

The term "label" refers to a display of written, printed or graphic matter upon the immediate container of an article, for example the written material displayed on a vial containing a pharmaceutically active agent.

The term "labeling" refers to all labels and other written, printed or graphic matter upon any article or any of its containers or wrappers or accompanying such article, for example, a package insert or instructional videotapes or DVDs accompanying or associated with a container of a pharmaceutically active agent.

4.2 Embodiments of the Invention

The present invention is based, in part, on the discovery that compounds of the invention are effective for the treatment and prevention of hepatitis C infection in a subject in need thereof. Accordingly, the present invention provides methods of treating hepatitis C infection in a subject in need thereof. The present invention further provides methods of preventing hepatitis C infection in a subject in need thereof. In general, the methods of the invention comprise the step of administering to the subject in need thereof an amount of a compound of the invention effective for the treatment or prevention of the hepatitis C infection. Methods of treatment are described in detail in the sections below. The compound can be any compound of the invention as described in the sections below. In certain embodiments, the compound is in the form of a pharmaceutical composition or dosage form, as described in the sections below.

While not intending to be bound by any particular theory of operation, it is believed that compounds of the invention inhibit hepatitis C virus (HCV) replication by a mechanism distinct from that of current HCV therapy. Current therapy for HCV, as mentioned above, is coadministration of interferon and ribavirin. It is believed that the current therapy operates by modulation of the immune system of a subject to treat or prevent infection by HCV. It is believed that compounds of the present invention operate by modulating or inhibiting cellular processes critical for HCV replication in a host. Such mechanisms are discussed in the examples below. Operating by a novel mechanism, the compounds, compositions and methods of the invention offer a novel therapy for the treatment or prevention of HCV infection. As such they are advantageous for any subject infected with, or at risk for infection with, HCV and particularly for subjects that have not responded to current therapy.

In embodiments of the invention, the subject can be any subject infected with, or at risk for infection with, HCV. Infection or risk for infection can be determined according to any technique deemed suitable by the practitioner of skill in the art. Particularly preferred subjects are humans infected with HCV.

The HCV can be any HCV known to those of skill in the art. There are at least six genotypes and at least 50 subtypes of HCV currently known to those of skill in the art. The HCV can be of any genotype or subtype known to those of skill. In certain embodiments, the HCV is of a genotype or subtype not yet characterized. In certain embodiments, the subject is infected with HCV of a single genotype. In certain embodiments, the subject is infected with HCV of multiple subtypes or multiple genotypes.

In certain embodiments, the HCV is genotype 1 and can be of any subtype. For instance, in certain embodiments, the HCV is subtype 1a, 1b or 1c. It is believed that HCV infection of genotype 1 responds poorly to current interferon therapy. Methods of the present invention can be advantageous for therapy of HCV infection with genotype 1.

In certain embodiments, the HCV is other than genotype 1. In certain embodiments, the HCV is genotype 2 and can be of any subtype. For instance, in certain embodiments, the HCV is subtype 2a, 2b or 2c. In certain embodiments, the HCV is genotype 3 and can be of any subtype. For instance, in certain embodiments, the HCV is subtype 3a, 3b or 10a. In certain embodiments, the HCV is genotype 4 and can be of any subtype. For instance, in certain embodiments, the HCV is subtype 4a. In certain embodiments, the HCV is genotype 5 and can be of any subtype. For instance, in certain embodiments, the HCV is subtype 5a. In certain embodiments, the HCV is genotype 6 and can be of any subtype. For instance, in certain embodiments, the HCV is subtype 6a, 6b, 7b, 8b, 9a or 11a. See, e.g., Simmonds, 2004, *J Gen Virol.* 85:3173–88; Simmonds, 2001, *J. Gen. Virol.,* 82, 693–712, the contents of which are incorporated by reference in their entirety.

In certain embodiments of the invention, the subject has never received therapy or prophylaxis for HCV infection. In further embodiments of the invention, the subject has previously received therapy or prophylaxis for HCV infection. For instance, in certain embodiments, the subject has not responded to HCV therapy. Indeed, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for HCV infection but has failed show a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97–100% chance of not responding. Since the compounds of the present invention act by mechanism other than current HCV therapy, it is believed that compounds of the invention should be effective in treating such nonresponders.

In certain embodiments, the subject is a subject that discontinued HCV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, the present invention provides methods of treating or preventing HCV infection in subjects where the risk of neuropsychiatric events, such as depression, contraindicates treatment with current HCV therapy. The present invention also provides methods of treating or preventing HCV infection in subjects where a neuropsychiatric event, such as depression, or risk of such indicates discontinuation of treatment with current HCV therapy. The present invention further provides methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects are include bone marrow suppression, neutropenia and thrombocytopenia. Furthermore, ribavirin is toxic to red blood cells and is associated with hemolysis. Accordingly, the present invention also provides methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments the subject has received HCV therapy and discontinued that therapy prior to administration of a method of the invention. In further embodiments, the subject has received therapy and continues to receive that therapy along with administration of a method of the invention. The methods of the invention can be co-administered with other therapy for HCV according to the judgment of one of skill in the art. In advantageous embodiments, the methods or compositions of the invention can be co-administered with a reduced dose of the other therapy for HCV.

In certain embodiments, the present invention provides methods of treating a subject that is refractory to treatment with interferon. For instance, in some embodiments, the subject can be a subject that has failed to respond to treatment with one or more agents selected from the group consisting of interferon, interferon α, pegylated interferon α, interferon plus ribavirin, interferon α plus ribavirin and pegylated interferon α plus ribavirin. In some embodiments, the subject can be a subject that has responded poorly to treatment with one or more agents selected from the group consisting of interferon, interferon α, pegylated interferon α, interferon plus ribavirin, interferon α plus ribavirin and pegylated interferon α plus ribavirin.

In further embodiments, the present invention provides methods of treating HCV infection in subjects that are pregnant or might get pregnant since current therapy is also contraindicated in pregnant women.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, *World J Gastroenterol* 8:577–57. The methods of the invention can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, *J Infect Dis* 179:1254–1258. Advantageously, compounds of the invention have been shown to suppress HIV in HIV subjects. See, e.g., U.S. Pat. Nos. 5,977,067; 5,994,299, 5,948,884 and 6,583,265 and PCT publication nos. WO99/32512, WO99/67280, the contents of which are hereby incorporated by reference in their entireties. Thus, in certain embodiments, the present invention provides methods of treating or preventing HIV infection and HCV infection in subjects in need thereof.

In certain embodiments, the methods or compositions of the invention are administered to a subject following liver transplant. Hepatitis C is a leading cause of liver transplantation in the U.S, and many subjects that undergo liver transplantation remain HCV positive following transplantation. The present invention provides methods of treating such recurrent HCV subjects with a compound or composition of the invention. In certain embodiments, the present invention provides methods of treating a subject before, during or following liver transplant to prevent recurrent HCV infection.

4.2.1 Compounds of the Invention

In certain embodiments, the present invention provides methods of treating or preventing hepatitis C infection in a subject in need thereof by administering to the subject an effective amount of a compound of the invention. In certain embodiments, the compound of the invention is a cyclosporin derivative effective for the treatment or prevention of hepatitis C infection in a subject in need thereof. Unless noted otherwise, the term "cyclosporin" as used herein refers to the compound cyclosporin A as known to those of skill in the art. See, e.g., Ruegger et al., 1976, *Helv. Chim. Acta.* 59:1075–92; Borel et al., 1977, *Immunology* 32:1017–25; the contents of which are hereby incorporated by reference in their entireties. The term "cyclosporin derivative" refers to any cyclosporin derivative with activity against hepatitis C infection, whether the derivative is natural, synthetic or semi-synthetic.

In particular embodiments, the cyclosporin derivative differs from cyclosporin A at the third position, i.e. the N-methyl glycine position, known to those of skill in the art. In certain embodiments, the cyclosporin derivative is a 3-ether cyclosporin. In further embodiments, the cyclosporin derivative is a 3-thioether cyclosporin. The cyclosporin derivative can further comprise other cyclosporin modifications known to those of skill in the art. In advantageous embodiments, the cyclosporin further comprises a 4-gamma-hydroxymethylleucine residue. Accordingly, in certain embodiments, the cyclosporin derivative is a 3-ether, 4-gamma-hydroxymethylleucine. In further embodiments, the cyclosporin derivative is a 3-thioether, 4-gamma-hydroxymethylleucine.

In certain embodiments, the present invention provides methods of treating or preventing hepatitis C infection in a subject comprising administering to the subject a therapeutically or prophylactically effective amount of a cyclosporin derivative of general formula (I), or a pharmaceutically acceptable salt or solvate thereof:

In certain embodiments, when X is sulfur preferably $R^1$ is selected from the group consisting of N,N-dimethylaminoethyl, N,N-diethylaminoethyl, N-methyl-N-tert-butylaminoethyl and N-ethyl-N-tert-butylaminoethyl.

In certain embodiments, X is sulfur, $R^2$ is isobutyl and $R^1$ is selected from the group consisting of N,N-dimethylaminoethyl, N,N-diethylaminoethyl, N-methyl-N-tert-butylaminoethyl and N-ethyl-N-tert-butylaminoethyl.

In certain embodiments, X is sulfur, $R^2$ is 2-hydroxyisobutyl and $R^1$ is selected from the group consisting of N,N-dimethylaminoethyl, N,N-diethylaminoethyl, N-methyl-N-tert-butylaminoethyl and N-ethyl-N-tert-butylaminoethyl.

Further preferred compounds of formula (I) are those in which $R^1$ is straight- or branched chain alkyl containing from two to six carbon atoms optionally substituted by a group $R^3$; or straight- or branched chain alkenyl containing from two to four carbon atoms; and $R^3$ is hydroxy, —$NR^4R^5$ or methoxy.

Further preferred compounds of formula (I) are those in which each of $R^4$ and $R^5$, which may be the same or different, is hydrogen; straight- or branched-chain alkyl

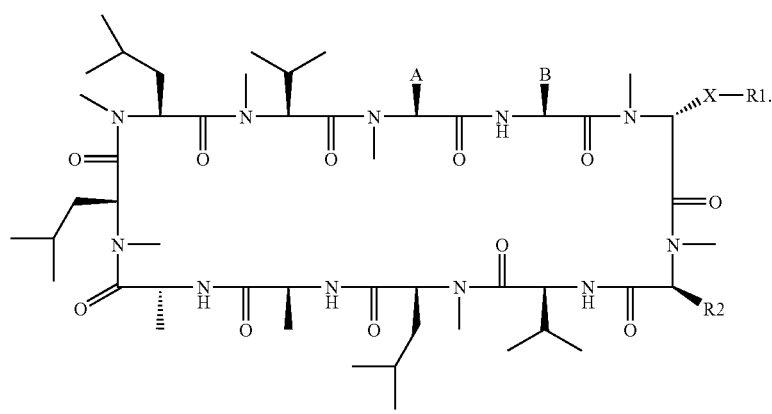

(I)

In formula (I), A, B, X, $R^1$ and $R^2$ are as defined above.

In certain embodiments, A is according to formula (IIa). In further embodiments, A is according to formula (IIb). In preferred embodiment, A is a residue of formula (IIa) above.

In preferred embodiments, B is ethyl.

Preferably $R^1$ is 2-aminoethyl, 2-aminopropyl, 2-monoalkylaminoethyl, 2-monoalkylaminopropyl, 2-dialkylaminoethyl 2-dialkylaminopropyl, 2-monocycloalkylaminoethyl, 2-monocycloalkylaminopropyl, 2-dicycloalkylaminoethyl or 2-dialkylaminopropyl wherein alkyl is straight- or branched-chain containing from one to four carbon atoms, and cycloalkyl contains from three to six carbon atoms.

In a further preferred embodiment $R^1$ is straight- or branched-chain alkyl containing from one to four carbon atoms (more preferably one or two carbon atoms), optionally substituted by one group $R^3$.

In certain embodiments, $R^2$ is isobutyl. In other embodiments, $R^2$ is 2-hydroxyisobutyl.

Preferably X is oxygen or sulfur. In certain embodiments, X is oxygen. In further embodiments, X is sulfur.

$R^3$ is preferably hydroxy or —$NR^4R^5$, wherein $R^4$ and $R^5$, which may be the same or different, each represent hydrogen or straight- or branched-chain alkyl containing from one to six carbon atoms (more preferably from one to four carbon atoms). In a further preferred embodiment $R^3$ is —$NR^4R^5$.

comprising from one to four carbon atoms, or $R^4$ and $R^5$, together with the nitrogen atom to which they are attached, form a saturated ring containing six ring atoms; the ring atoms other than the nitrogen atom being independently selected from carbon and oxygen.

In a further preferred embodiment $R^3$ is selected from the group consisting of halogen, hydroxy, carboxyl, alkoxycarbonyl, —$NR^4R^5$ and —$NR^6(CH_2)_mNR^4R^5$.

Preferably halogen is fluoro, chloro or bromo, and more preferably fluoro or chloro.

Compounds of formula (I) in which X is oxygen and $R^1$ is 2-methoxyethyl, or pharmaceutically acceptable salts thereof, are also preferred.

Compounds of formula (I) in which X is oxygen or sulphur and $R^1$ is propyl substituted by —$NR^4R^5$ or methoxy, or pharmaceutically acceptable salts thereof, are also preferred.

Among these more preferred compounds used in the method of the present invention, are the cyclosporin derivatives listed below:
3-methoxycyclosporin;
3-ethoxycyclosporin;
3-propoxycyclosporin;
3-isopropoxycyclosporin;
3-(2-aminoethoxy)cyclosporin;
3-(2-N-methylaminoethoxy)cyclosporin;

3-(2-N-ethylaminoethoxy)cyclosporin;
3-(2-dimethylaminoethoxy)cyclosporin;
3-(2-diethylaminoethoxy)cyclosporin;
3-(2-tert-butyl-methylaminoethoxy)cyclosporin;
3-(2-tert-butyl-ethylaminoethoxy)cyclosporin;
3-[(R)-2-(N,N-dimethylamino)ethylthio-Sar]-4-[4'-hydroxy-MeLeu]-cyclosporin;
3-[(R)-2-(N,N-dimethylamino)ethylthio-Sar]-cyclosporin;
3-[(R)-2-(hydroxy)ethylthio-Sar]-4-[4'-hydroxy-MeLeu]-cyclosporin;
3-[(R)-2-(hydroxy)ethylthio-Sar]-cyclosporin;
3-[(R)-2-(N,N-diethylamino)ethylthio-Sar]-4-[4'-hydroxy-MeLeu]-cyclosporin;
3-[(R)-2-(N,N-diethylamino)ethylthio-Sar]-cyclosporin;
3-(sec-butoxy)cyclosporin;
3-[2-(1,4-dihydropyrid-1-yl)ethoxy)cyclosporin;

and their pharmaceutically acceptable salts.

Particularly preferred compounds useful in the method of the invention include the following:
Compound Name
A 3-methoxycyclosporin
B 3-(2-aminoethoxy)cyclosporin
C 3-(2-N,N-dimethylaminoethoxy)cyclosporin
D 3-(isopropoxy)cyclosporin
E 3-(2-ethylbutoxy)cyclosporin
F 3-(2,2-dimethylpropoxy)cyclosporin
G 3-(2-hydroxyethoxy)cyclosporin
H 3-(3-hydroxypropoxy)cyclosporin
I 3-[2-(N-methylamino)ethoxy]cyclosporin
J 3-[2-(N-methyl-N-isopropylamino)ethoxy]cyclosporin
K 3-[2-(piperidin-1-yl)ethoxy]cyclosporin
L 3-[2-(N-morpholine)ethoxy)cyclosporin
M 3-ethoxycyclosporin
N 3-(2-methoxyethylthio)-4-(gamma-hydroxymethylleucine)cyclosporin
O 3-[(R)-2-(N,N-dimethylamino)ethylthio-Sar]-4-(gamma-hydroxymethylleucine)cyclosporin
P 3-ethylthiocyclosporin
Q 3-propenylthiocyclosporin
R 3-[(2-methoxy)ethylthio]cyclosporin
S 3-(methylthio)-4-(gamma-hydroxymethylleucine)cyclosporin
T 3-(methoxy)-4-(gamma-hydroxymethylleucine)cyclosporin
U 3-(prop-2-ene-1-oxy)-4-(gamma-hydroxymethylleucine)cyclosporin
V 3-(isopropoxy)-4-(gamma-hydroxymethylleucine)cyclosporin
W 3-(ethoxy)-4-(gamma-hydroxymethylleucine)cyclosporin
X 3-[2-(methoxy)ethoxy]-4-(gamma-hydroxymethylleucine)cyclosporin
Y 3-[3-(methoxy)propoxy]-4-(gamma-hydroxymethylleucine)cyclosporin The Compound Letters A to Y are used hereafter.

In particular embodiments, the present invention provides a method of treating or preventing hepatitis C virus infection in a subject by administering, to a subject in need thereof, an effective amount of a compound of the invention selected from the group consisting of compounds A to Y, or a pharmaceutically acceptable salt thereof.

Compound O, or a pharmaceutically acceptable salt thereof, is particularly preferred, due to its high level of activity and its toxicological profile, as described in the examples below.

In certain embodiments, cyclosporin derivatives according to the invention in which $R^1$ is alkyl substituted by one or more groups $R^3$, where $R^3$ is —$NR^4R^5$ or —$NR^6(CH_2)_m NR^4R^5$ and $R^{4, R5}$ and $R^6$ are as defined above, can be converted into addition salts with acids by known methods. It is understood that these salts also come within the scope of the present invention. Exemplary salts of the invention, and methods of their preparation, are described in the sections below.

In useful embodiments of the invention, the compound is in a pure form. Purity can be any purity known to those of skill in the art such as absolute purity, stereochemical purity or both. In certain embodiments, the compound of the invention is at least 80%, 85%, 90%, 91%, 92%, 93%, 94%, 95%, 96%, 97%, 98% or 99% pure. In certain embodiments, the compound of the invention is at least 90% pure. In further embodiments, of the invention, the compound is at least 98% pure. Methods of purifying compounds of the invention are described below.

4.2.2 Preparation of Compounds of the Invention

The compounds of the invention can be prepared, isolated or obtained by any method apparent to those of skill in the art. Exemplary methods of preparation are described in detail in the examples below.

In addition, cyclosporins substituted in the 3-position by thioether or ether groups can be prepared according to methods described in U.S. Pat. Nos. 5,977,067; 5,994,299, 5,948,884 and 6,583,265 and in PCT publication nos. WO99/32512, WO99/67280. The contents of these references are hereby incorporated by reference in their entireties.

Compounds can be purified after synthesis by any technique apparent to those of skill in the art for purifying cyclosporin derivatives. In certain embodiments, a compound of the invention is purified by chromatography. For instance, a compound of the invention can be purified using high-performance liquid chromatography (HPLC). An useful example of the HPLC purification is as follows: An HPLC column of dimensions 10 mm (d)×50 mm (l) containing a 5-μm reverse-phase stationary phase (octadecyl-silane or octa-silane) is equilibrated with a mobile phase comprising 0.1% formic acid, 50 to 90% water, and 50 to 10% acetonitrile. Importantly, the column is heated to at least 65° C., or potentially up to 85° C. The mobile phase flows at 10 to 16 mL/minute and is heated to 60° C. Approximately 5 to 25 mg of a cyclosporin derivative is loaded on the column in 0.1 to 0.8 mL of a solvent, preferably dimethylsulfoxide. The mobile phase flow is maintained, and its composition is adjusted in a linear gradient up to 90% or 100% acetonitrile over a period of 20 to 60 minutes. Compound peaks are detected using evaporative light scattering detection and/or variable-ultraviolet detection at a wavelength setting of 205 to 215 nm. Compound peaks are collected in the mobile phase which is removed in vacuo; samples are thoroughly dried in vacuo and analyzed by NMR, IR, and HPLC-MS to determine identity and purity.

4.2.3 Pharmaceutical Salts of Compounds of the Invention

As discussed above, a cyclosporin derivative of the invention can be in a neutral form, or in a salt form. The salt form can be any salt form known to those of skill in the art. Particularly useful salt forms are those that are coordinated with phosphate, citrate, acetate, chloride, methanesulfonate or propionate.

Where a compound of the present invention, e.g. a compound of the invention, is substituted with a basic moiety, an acid addition salt can be formed. The acid which can be used to prepare an acid addition salt includes preferably that which produces, when combined with the free base, a pharmaceutically acceptable salt, that is, a salt whose anion is non-toxic to a subject in the pharmaceutical doses of the salt. Pharmaceutically acceptable salts within the scope of the invention are those derived from the following acids: mineral acids such as hyrochloric acid, hydrobromic acid, sulfuric acid, phosphoric acid, sulfamic acid and nitric acid; and organic acids such as acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids.

The corresponding acid addition salts include hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

According to a further feature of the invention, acid addition salts of the compounds of this invention can be prepared by reaction of the free base with the appropriate acid, by the application or adaptation of known methods. For example, the acid addition salts of the compounds of this invention can be prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention, e.g. compounds of the invention, can be regenerated from the salts by the application or adaptation of known methods. For example, parent compounds of the invention can be regenerated from their acid addition salts by treatment with an alkali, e.g., aqueous sodium bicarbonate solution or aqueous ammonia solution.

Where a compound of the invention, e.g. a compound of the invention, is substituted with an acid moiety, base addition salts can be formed. Pharmaceutically acceptable salts, including for example alkali and alkaline earth metal salts, within the scope of the invention are those derived from the following bases: sodium hydride, sodium hydroxide, potassium hydroxide, calcium hydroxide, magnesium hydroxide, aluminum hydroxide, lithium hydroxide, zinc hydroxide, barium hydroxide, and organic amines such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Metal salts of compounds of the present invention, e.g. compounds of the invention, can be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention, e.g. compounds of the invention, can be obtained by contacting an amine in an aqueous or organic solvent with the free acid form of the compound. Suitable aqueous solvents include water and mixtures of water with alcohols such as methanol or ethanol, ethers such as tetrahydrofuran, nitrites, such as acetonitrile, or ketones such as acetone. Amino acid salts may be similarly prepared.

The base addition salts of the compounds of this invention, e.g. compounds of the invention, can be regenerated from the salts by the application or adaptation of known methods. For example, parent compounds of the invention can be regenerated from their base addition salts by treatment with an acid, e.g., hydrochloric acid.

4.2.4 Pharmaceutical Compositions and Methods of Administration

The cyclosporin derivatives used in the method of the present invention are preferably provided using pharmaceutical compositions containing at least one compound of general formula (I), if appropriate in the salt form, either used alone or in the form of a combination with one or more compatible and pharmaceutically acceptable carriers, such as diluents or adjuvants, or with another anti-HCV agent. In clinical practice the cyclosporin derivatives of the present invention may be administered by any conventional route, in particular orally, parenterally, rectally or by inhalation (e.g. in the form of aerosols). The cyclosporin derivatives of the present invention are preferably administered orally.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In a preferred embodiment, a composition of the invention is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of the invention, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions of the invention can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent preferably in purified form, together with a suitable amount of carrier so as to provide the form for proper administration to the subject. The formulation should suit the mode of administration. In a preferred embodiment, the pharmaceutical compositions or single unit dosage forms are sterile and in suitable form for administration to a subject, preferably an animal subject, more preferably a mammalian subject, and most preferably a human subject.

A pharmaceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intrasynovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms of the invention will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms of the invention comprise a compound of the invention, or a pharmaceutically acceptable salt, solvate or hydrate thereof lie within the range of from about 0.1 mg to about 1000 mg per day, given as a single once-a-day dose in the morning but preferably as divided doses throughout the day taken with food. Particular dosage forms of the invention have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active cyclosporin.

4.2.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In preferred embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

4.2.5 Delayed Release Dosage Forms

Active ingredients such as the compounds of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

4.2.6 Parenteral Dosage Forms

Although solid, anhydrous oral dosage forms are preferred, the present invention also provides parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are preferably sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4.2.7 Transdermal, Topical & Mucosal Dosage Forms

Although solid, anhydrous oral dosage forms are preferred, the present invention also provides transdermal, topical, and mucosal dosage forms. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

4.2.8 Dosage and Unit Dosage Forms

In human therapeutics, the doctor will determine the posology which he considers most appropriate according to a preventive or curative treatment and according to the age, weight, stage of the infection and other factors specific to the subject to be treated. Generally, doses are from about 1 to about 1000 mg per day for an adult, or from about 5 to about 250 mg per day or from about 10 to 50 mg per day for an adult. In certain embodiments, doses are from about 5 to about 400 mg per day, and more preferably 25 to 200 mg per day per adult. Dose rates of from about 50 to about 500 mg per day are also preferred.

In further aspects, the present invention provides methods of treating or preventing hepatitis C virus infection in a subject by administering, to a subject in need thereof, an effective amount of a compound of the invention, or a pharmaceutically acceptable salt thereof, with a high therapeutic index against hepatitis C virus. The therapeutic index can be measured according to any method known to those of skill in the art, such as the method described in the examples below. In certain embodiments, the therapeutic index is the ratio of a concentration at which the compound is toxic, to the concentration that is effective against hepatitis C virus. Toxicity can be measured by any technique known to those of skill including cytotoxicity (e.g. $IC_{50}$ or $IC_{90}$) and lethal dose (e.g. $LD_{50}$ or $LD_{90}$). Likewise, effective concentrations can be measured by any technique known to those of skill including effective concentration (e.g. $EC_{50}$ or $EC_{90}$) and effective dose (e.g. $ED_{50}$ or $ED_{90}$). Preferably, similar measurements are compared in the ratio (e.g. $IC_{50}/EC_{50}$, $IC_{90}/EC_{90}$, $LD_{50}/ED_{50}$ or $LD_{90}/ED_{90}$). In certain embodiments, the therapeutic index can be as high as 2.0, 5.0, 10.0, 15.0, 20.0, 25.0, 50.0, 75.0, 100.0, 125.0, 150.0 or higher.

The amount of the compound or composition of the invention which will be effective in the prevention, treatment, management, or amelioration of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions of the invention, the dosage administered to a subject is typically 0.140 mg/kg to 3 mg/kg of the subject's body weight, based on weight of the active compound. Preferably, the dosage administered to a subject is between 0.20 mg/kg and 2.00 mg/kg, or between 0.30 mg/kg and 1.50 mg/kg of the subject's body weight.

In general, the recommended daily dose range of a composition of the invention for the conditions described herein lie within the range of from about 0.1 mg to about 1000 mg per day, given as a single once-a-day dose or as divided doses throughout a day. In one embodiment, the daily dose is administered twice daily in equally divided doses. Specifically, a daily dose range should be from about 10 mg to about 200 mg per day, more specifically, between about 10 mg and about 150 mg per day, or even more specifically between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition of the invention are also encompassed by the above described dosage amounts and dose frequency schedules. Further, when a subject is administered multiple dosages of a composition of the invention, not all of the dosages need be the same. For example, the dosage administered to the subject may be increased to improve the prophylactic or therapeutic effect of the composition or it may be decreased to reduce one or more side effects that a particular subject is experiencing.

In a specific embodiment, the dosage of the composition of the invention or a composition of the invention, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition of the invention or a composition of the invention administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 mg to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition of the invention followed by one or more maintenance doses. In such embodiments, the loading dose can be, for instance, about 60 to about 400 mg per day, or about 100 to about 200 mg per day for one day to five weeks. The loading dose can be followed by one or more maintenance doses. Each maintenance does can be, independently, about from about 10 mg to about 200 mg per day, more specifically, between about 25 mg and about 150 mg per day, or even more specifically between about 25 and about 80 mg per day. Maintenance doses are preferably administered daily and can be administered as single doses, or as divided doses.

In certain embodiments, a dose of a compound or composition of the invention can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition of the invention is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations of about 1200 to about 8000 ng/mL, or about 2000 to about 4000 ng/mL for one to five days. Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, the present invention provides unit dosages comprising a compound of the invention, or a pharmaceutically acceptable salt thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

4.3 Kits

The invention also provides kits for use in methods of treatment or prophylaxis of HCV infection. The kits can include a pharmaceutical compound or composition of the invention and instructions providing information to a health care provider regarding usage for treating or preventing a bacterial infection. Instructions may be provided in printed form or in the form of an electronic medium such as a floppy disc, CD, or DVD, or in the form of a website address where such instructions may be obtained. A unit dose of a compound or composition of the invention can include a dosage such that when administered to a subject, a therapeutically or prophylactically effective plasma level of the compound or composition can be maintained in the subject for at least 1 days. In some embodiments, a compound or composition of the invention can be included as a sterile aqueous pharmaceutical composition or dry powder (e.g., lyophilized) composition. In one embodiment, the compound is according to formula (I).

In some embodiments, suitable packaging is provided. As used herein, "packaging" refers to a solid matrix or material customarily used in a system and capable of holding within fixed limits a compound or composition of the invention suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Kits of the invention may also comprise, in addition to the compound or composition of the invention, other compounds or compositions for use with compound or composition as described in the methods above.

The following Examples illustrate the synthesis of representative cyclosporin derivatives used in the present invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention

5. EXAMPLES

5.1 Example 1

3-Methoxycyclosporin

A solution of 3-(mercaptobenzthiazol-2-ylthio)cyclosporin (0.4 g, 0.28 mmol) and camphor sulfonic acid (0.7 g, 3 mmol) in dry tetrahydofuran and dry methanol was heated at 50° C. for 2 h. The mixture was allowed to cool to room temperature and saturated sodium bicarbonate, ether and water were added. The layers were separated and the aqueous phase extracted with diethyl ether. The combined organic extracts were dried over anhydrous magnesium sulfate, filtered and evaporated to dryness. Repeated chromatography on silica gel eluting with a mix of dichloromethane and ethyl acetate yielded 120 mg of 3-methoxycyclosporin (compound A).

NMR signals for this compound in deuterochloroform are at 5.83 ppm (sarcosine H), 3.49 ppm (methoxy $CH_3$), 83.5 ppm (sarcosine C) and 58.7 ppm (methoxy $CH_3$).

5.2 Example 2

3-(2-Aminoethoxy)cyclosporin

To a solution of 3-(N-Fmoc-2-aminoethoxy) cyclosporin (0.52 g, 0.35 mmol) in dimethylformamide (16 ml) was added piperidine (4 ml). The mixture was stirred under nitrogen for 1.25 h. The resultant mixture was diluted with ethyl acetate (25 ml) and water (25 ml). The organic phase was washed with water (20 ml), brine (2×10 ml), dried over anhydrous magnesium sulfate, filtered and evaporated to dryness. The resultant material was purified by repeated silica gel chromatography eluting with a gradient of methanol/ethyl acetate through to 100% methanol yielding 3-(2-aminoethoxy)cyclosporin (Compound B) as a white gum (130 mg). NMR signals for this compound in deuterochloroform are at 5.95 ppm (sarcosine H).

Salt Formation

Compound B (130 mg) was dissolved in dichloromethane and treated with a solution of methanesulfonic acid (1 ml of 0.1 M solution in dichloromethane); stirring was continued for 10 minutes. The solvent was evaporated and the residue triturated with diethyl ether to give a white solid (120 mg).

5.3 Example 3

3-(2-dimethylaminoethoxy)cyclosporin

A solution of 3-(2-aminoethoxy)cyclosporin (0.375 g, 0.3 mmol), formalin (0.8 mmol) and formic acid (1.33 mmol) in 1,4-dioxane was heated at 80° C. for 5 h. The mixture was allowed to cool to room temperature and diluted with saturated sodium bicarbonate. The resultant mixture was extracted with dichloromethane, the combined organic extracts were dried over anhydrous magnesium sulfate, filtered and evaporated. The residue was purified by repeated column chromatography on silica gel eluting with a gradient of methanol/dichloromethane to 100% methanol to give 3-(2-dimethylaminoethoxy)cyclosporin (Compound C, 230 mg).

NMR signals for this compound in deuterochloroform are at 6.01 ppm (sarcosine H) and 82.6 ppm (sarcosine C).

Salt Formation

To solution of compound C (194 mg) in tert-butylmethyl ether and methanol was added a solution of hydrochloric acid (2 ml of 2.0M solution in ether). The resultant mixture was stirred for 1 h and then the solvents were evaporated. The residue was triturated with ether to give a pale yellow solid (154 mg).

5.4 Example 4

3-Methoxy-4-(gamma-hydroxymethylleucine)-cyclosporin

3-Methoxy-4-(gamma-hydroxymethylleucine)-cyclosporin:

To a solution of 1,4-di-acetyl-3-methoxy-4-(gamma-hydroxymethylleucine)-cyclosporin (275 mg) in methanol (15 mL) was added 25 wt % sodium methoxide in methanol (0.12 mL) and the resulting mixture was stirred at room temperature for 24 h under nitrogen. Methanol was removed under reduced pressure and the residue was diluted with ethyl acetate (50 mL), washed with saturated ammonium chloride (30 mL), brine (30 mL), and dried over anhydrous sodium sulfate. After solvent removal, the residue was purified using preparative liquid chromatography to yield 33 mg the title compound (Compound T).

NMR signals for this compound in deuterochloroform are at (ppm) 5.80 (singlet, sarcosine H), and four doublet NH signals at 7.14, 7.39, 7.69, and 7.96. LCMS (ESI): calcd for $C_{63}H_{113}N_{11}O_{14}$: 1247, found 1248.5 $(M+H)^+$.

5.5 Examples 5–13

3-Ether cyclosporins

The following compounds of formula (I) above in which A is a residue of formula (IIa) above, B is ethyl, X is oxygen and $R^2$ is isobutyl were also prepared by proceeding in a similar manner described in the specified Example or Reference Example for each product:

| Cmpd | $R^1$ | Method Example | Molecular Mass M + H (m/z) | $^1$H-NMR Sarcosine Resonance (ppm) |
|---|---|---|---|---|
| D | $CH(CH_3)_2$ | 1 | 1260.5 | 6.09 |
| E | $CH_2CH(Et)_2$ | 1 | 1302.7 | 5.87 |
| F | $CH_2C(CH_3)_3$ | 1 | 1288.7 | 5.89 |
| G | $CH_2CH_2OH$ | 1 | 1262.6 | 6.02 |
| H | $CH_2CH_2CH_2OH$ | 1 | 1276.6 | 5.94 |
| I | $CH_2CH_2NHMe$ | 2 | 1275.6 | 5.96 |
| J | $CH_2CH_2NMe(Pr-i)$ | 1 | 1317.7 | 5.97 |
| K | $CH_2CH_2N(CH_2)_5$ | 1 | 1329.7 | 6.02 |
| L | $CH_2CH_2N(CH_2CH_2)_2O$ | 1 | 1317.6 | 6.06 |
| M | $CH_2CH_3$ | Reference Example 1 | 1246.6 | 5.83 |
| U | $CH_2CH=CH_2$ | 5 | 1274.6 | 5.92 |
| V | $CH_2CH_3$ | 5 | 1262.6 | 5.89 |
| W | $CH(CH_3)_2$ | 5 | 1276.6 | 6.00 |
| X | $CH_2CH2OCH_3$ | 5 | 1292.6 | 6.01 |
| Y | $CH_2CH_2CH_2OCH_3$ | 5 | 1306.6 | 5.88 |

5.6 Example 14

3-(2-Methoxyethylthio)-4-(gamma-hydroxymethylleucine)cyclosporin

Liquid ammonia (30 mL) was condensed in a flask under nitrogen. Sodium amide (1.0 g) was added followed by a solution of 4-(gamma-hydroxymethylleucine)-cyclosporin (1.22 g, 1.0 mmol) in tert-butylmethyl ether (20 mL). The mixture was stirred at −35° C. for 90 minutes. 2-Methoxyethyl disulfide (5.9 g) was added and stirring is continued for another 2 hrs at −35° C. Solid ammonium chloride (1.5 g) was added and the mixture was stirred at −33° C. for 10 minutes. After warming up to room temperature, the mixture was diluted with tert-butylmethyl ether, washed with water, brine, and dried over anhydrous sodium sulfate. After solvent removal, the residue was purified using silica gel column chromatography, eluting first with ethyl acetate/heptane then methanol/ethyl acetate, to yield 500 mg of 3-(2-methoxyethylthio)-4-(gamma-hydroxymethylleucine) cyclosporin (Compound N). NMR signals for this compound in deuterochloroform are at (ppm): 5.97 (singlet, sarcosine H), and four doublet NH signals at 7.14, 7.47, 7.62, and 7.92. LCMS (ES): calculated for $C_{65}H_{117}N_{11}O_{14}S$: 1307, found 1308.6 $(M+H)+$.

5.7 Examples 15–19

3-Thioether cyclosporins

The following compounds of formula (I) above in which A is a residue of formula (IIa) above, B is ethyl and X is sulfur were also prepared by proceeding in a similar manner described in the specified Example or Reference Example for each product:

| Cmpd | R¹ | R² | Method Example | Molecular Mass M⁺H (m/z) | ¹H-NMR Sarcosine Resonance (ppm) |
|---|---|---|---|---|---|
| O | $CH_2CH_2N(CH_3)_2$ | 2-hydroxyisobutyl | 15 | 1321.7 | 6.00 |
| P | $CH_2CH_3$ | Isobutyl | Reference Example 1 | 1262.6 | 5.85 |
| Q | $CH_2CH{=}CH_2$ | Isobutyl | Reference Example 1 | 1274.6 | 5.79 |
| R | $CH_2CH_2OCH_3$ | Isobutyl | 15 | 1292.6 | 5.98 |
| S | CH3 | 2-hydroxyisobutyl | 15 | 1264.6 | 5.73 |

5.8 Reference Example 1

3-(Mercaptobenzthiazol-2-ylthio)cyclosporin

To a solution of lithium diisopropylamide (LDA) (10.0 mmol) in dry tetrahydrofuran at −70° C. under an inert atmosphere was added, drop wise, a solution of cyclosporin A (1.2 g, 1.0 mmol) in dry tetrahydrofuran, stirring was continued at −70° C. for 1 h, after this time solid bis-benzothiazole disulfide (5 g, 15 mmol) was added in one portion. The resultant suspension was allowed to warm to room temperature and stirred for 18 h. The mixture was filtered and the filtrate treated with water and evaporated to dryness. The residue was dissolved in ethyl acetate and washed with brine, dried over anhydrous magnesium sulfate, filtered and evaporated to dryness. The resultant brown gum (3.3 g) was purified by silica gel chromatography eluting with ethyl acetate/isohexane to yield 3-(mercaptobenzthiazol-2-ylthio)cyclosporin as a beige solid (0.33 g). NMR signals for this compound in deuterochloroform are at 6.98 ppm (sarcosine H).

5.9 Reference Example 2

3-(N-Fmoc-2-Aminoethoxy)-cyclosporin

To a solution of 3-(mercaptobenzthiazol-2-ylthio) cyclosporin (0.7 g, 0.5 mmol) in dry tetrahydrofuran was added camphor sulfonic acid (0.175 g, 0.75 mmol) and (2-Hydroxy-ethyl)-carbamic acid 9H-fluoren-9-ylmethyl ester (1.7 g, 6 mmol), the resultant solution was heated at 50° C. for 4.5 h. The reaction mix was allowed to cool to room temperature and was diluted with ethyl acetate (25 ml). The solution was washed with saturated sodium sulfate (20 ml), brine (20 ml), dried over anhydrous magnesium sulfate, filtered and evaporated to dryness. The residue was purified by column chromatography on silica gel eluting with ethyl acetate/dichloromethane yielding 3-(N-Fmoc-2-aminoethoxy)cyclosporin as a gum (0.52 g). NMR signals for this compound in deuterochloroform are at 5.9 ppm (sarcosine H).

5.10 Reference Example 3

(2-Hydroxy-ethyl)-carbamic acid 9H-fluoren-9-ylmethyl ester

To a stirred mixture of ethanotamine (0.49 g, 8 mmol), tetrahydrofuran, water and sodium bicarbonate (1.5 g, 18 mmol) at 6° C., was added a solution 9-fluorenylmethyl-chloroformate (2.27 g, 8.8 mmol) in tetrahydrofuran in one portion, stirring was continued for 1 h allowing the mixture to warm to room temperature. The mixture was diluted with water and extracted with ethyl acetate. The combined organic extracts were dried over anhydrous magnesium sulfate filtered and evaporated to a crude product. The crude product was re-crystallised from dichloromethane to give (2-hydroxy-ethyl)-carbamic acid 9H-fluoren-9-ylmethyl ester as a white solid (1.2 g).

5.11 Reference Example 4

1,4-Di-acetyl-3-methoxy-4-(gamma-hydroxymethylleucine)-cyclosporin

To a solution of 1,3,4-Tri-acetyl-4-(gamma-hydroxymethylleucine)-cyclosporin (295 mg) in methanol (5 mL) was added camphorsulfonic acid (55 mg); the resulting mixture was stirred at 50° C. for 5 h under nitrogen. Methanol was removed under reduced pressure and the residue was diluted with ethyl acetate (50 mL), washed with saturated sodium bicarbonate (30 mL), brine (30 mL), and dried over anhydrous sodium sulfate. After solvent removal, 275 mg of the title compound was obtained and used for the next step without further purification.

NMR signals for this compound in deuterochloroform are at (ppm) 1.92 (singlet, OAc), 2.00 (singlet, OAc), 5.71 ppm (singlet, sarcosine H), and four doublet NH signals 7.33, 7.43, 8.03, and 8.51. LCMS (ESI): calcd for $C_{63}H_{113}N_{11}O_{14}$: 1331, found 1332.6 (M+H)⁺.

5.12 Reference Example 5

1,3,4-Tri-acetyl-4-(gamma-hydroxymethylleucine)-cyclosporin

To a solution of 1,4-di-acetyl-3-phenylthio-4-(gamma-hydroxymethylleucine)-cyclosporin (389 mg) in glacial acetic acid (8 mL) was added mercuric acetate (389 mg) and the resulting mixture was stirred at 50° C. for 3 h under nitrogen. Acetic acid was removed under reduced pressure and the residue was diluted with ethyl acetate (50 mL), washed with saturated sodium bicarbonate (30 mL), brine (30 mL), and dried over anhydrous sodium sulfate. After solvent removal, the residue was purified using silica gel column chromatography, eluting first with ethyl acetate/heptane (30:70), then methanol/ethyl acetate (0.2/100), to yield 280 mg of the title compound.

5.13 Reference Example 6

1,4-Di-acetyl-3-phenylthio-4-(gamma-hydroxymethylleucine)-cyclosporin

To a solution of 3-phenylthio-4-(gamma-hydroxymethylleucine)-cyclosporin (550 mg) in dry dichloromethane (10 mL) were added 4-dimethylaminopyridine (310 mg), triethylamine (0.35 mL), and acetic anhydride (0.16 mL) in this order and the resulting mixture was stirred at room temperature for 60 h under nitrogen. It was diluted with ethyl acetate (50 mL), washed with water (50 mL), 1.0 N HCl (50 mL), saturated sodium bicarbonate (50 mL), brine (50 mL), and dried over anhydrous sodium sulfate. After solvent removal and drying under vacuum, 389 mg of the title compound was obtained.

NMR signals for this compound in deuterochloroform are at (ppm): 2.00 (3H, singlet, OAc), 2.04 (3H, singlet, OAc), 6.11 (1H, singlet, sarcosine H), 7.20–7.37 (6H, multiplet, NH and phenyl), and three doublet NH signals 7.44, 8.03, and 8.52.

5.14 Reference Example 7

3-Phenylthio-4-(gamma-hydroxymethylleucine)cyclosporin

Liquid ammonia (30 mL) was condensed in a flask under nitrogen. Sodium amide (1.0 g) was added followed by a solution of 4-(gamma-hydroxymethylleucine)-cyclosporin (1.22 g, 1.0 mmol) in tert-butylmethyl ether (15 mL). The mixture was stirred at −35° C. for 90 min. Then, a solution of diphenyl disulfide (4.4 g, 20 mmol) in tert-butylmethyl ether (15 mL) was added and stirring is continued for another 2 h at −35° C. Solid ammonium chloride (1.5 g) was added and the mixture was stirred at −33° C. for 10 minutes. After warming up to room temperature, the mixture was diluted with tert-butylmethyl ether (50 mL), washed with water (50 mL), brine (50 mL), and dried over anhydrous sodium sulfate. After solvent removal, the residue was purified using silica gel column chromatography, eluting first with ethyl acetate/heptane (30:70), then methanol/ethyl acetate (0.2:100), to yield 550 mg of the title compound.

NMR signals for this compound in deuterochloroform are at (ppm) 6.12 (1H, singlet, sarcosine H), 7.33 (5H, multiplet, Ph), and four doublet NH signals, 7.14, 7.39, 7.65, and 7.96.

5.15 Example 20

Salts of [(R)-2-(N,N-dimethylamino)ethylthio-Sar]3 [4'-hydroxy-MeLeu]4 cyclosporin (Compound O)

The instant example demonstrates pharmaceutically acceptable salts of the invention that display advantageous solubility for use in the methods of the invention.

[(R)-2-(N,N-Dimethylamino)ethylthio-Sar]3 [4'-hydroxy-MeLeu]4 cylcosporin A (1.0 g) was dissolved in 10 mL of ethyl ether. The corresponding acid (1.0 equiv) was added and stirred at 25° C. for 2 h. The precipitate was collected by filtration and washed with cold ether, dried under vacuum and analyzed. In the examples of the acetate and propionate salts 10 mL of heptane was added to the ether solution to promote precipitation. The solubility of each salt in biological buffer, namely Dulbecco's Phosphate Buffered Saline (PBS), was determined using turbidimetric titration (Schote, et al., 2002. *J Pharm Sciences* 91(3):856). The pH 7.2 buffer has physiological concentrations of calcium, magnesium, sodium, potassium, phosphate, and chloride. The solubility of cyclosporin in PBS is 0.015 to 0.020 mM, whereas the salts are soluble in the range of 0.45 to 0.65 mM. The following salts of compound O were prepared:

| Salt | Melting Point (° C.) | 1H-NMR Sarcosine Resonance (ppm) | PBS Solubility mM |
| --- | --- | --- | --- |
| Phosphate | 167–169 | 5.84 | 0.534 |
| Citrate | 148–150 | 5.91 | 0.532 |
| Acetate | 117–119 | 5.92 | 0.612 |
| HCl | 175–178 | 5.81 | 0.497 |
| Methanesulfonate | 150–155 | 5.82 | 0.537 |
| Propionate | 110–112 | 5.95 | 0.522 |

5.16 Example 21

HCV Activity

The instant example demonstrates that compounds of the invention are effective against HCV infection. In addition, the instant example demonstrates that compounds of the invention show advantageous efficacy, or cytotoxicity, or both when compared to cyclosporin A.

The compounds of the present invention (as salts prepared as described in Examples 1 to 21) were tested for activity against HCV using the methods adapted from those described by Kriger et al., 2001, *Journal of Virology*, 75:4614–4624, Pietschmann et al., 2002, *Journal of Virology* 76:4008–4021, and using HCV RNA constructs as described in U.S. Pat. No. 6,630,343. The contents of these references are hereby incorporated by reference in their entireties.

Compounds were examined in the human hepatoma cell line ET (lub ubi neo/ET), a HCV RNA replicon containing a stable luciferase (LUC) reporter. The HCV RNA replicon ET contains the 5' end of HCV (with the HCV Internal Ribosome Entry Site (IRES) and the first few amino acids of the HCV core protein) which drives the production of a firefly luciferase (LUC), ubiquitin, and neomycin phosphotransferase (NeoR) fusion protein. Ubiquitin cleavage releases the LUC and NeoR proteins. The EMCV IRES element controls the translation of the HCV, structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The activity of the LUC reporter is directly proportional to HCV replication levels and positive-control antiviral compounds produce a reproducible antiviral response using the LUC endpoint.

The compounds were dissolved in DMSO at five half-log concentrations each, ranging from either 0.02 to 2.0 µM, 0.03 to 3 µM, 2.0 to 20 µM, or 1 to 100 µM. Subconfluent cultures of the ET line were plated out into 96 well plates dedicated for the analysis of cell numbers (cytotoxicity) or antiviral activity and the next day the compounds were added to the appropriate wells. The cells were processed 72 h later when the cells were still subconfluent. Antiviral activity was expressed as $EC_{50}$ and $EC_{90}$, the effective concentration of compound that reduced viral replication by 50% and 90%, respectively. Compound $EC_{50}$ and $EC_{90}$ values were derived from HCV RNA levels assessed as HCV RNA replicon derived LUC activity. Cytotoxicity was expressed as $IC_{50}$ and $IC_{90}$, the concentration of compound that inhibited cell viability by 50% and 90%, respectively. Compound $IC_{50}$ and $IC_{90}$ values were calculated using a colorimetric assay as an indication of cell numbers and cytotoxicity. The activity of the LUC reporter is directly proportional to HCV RNA levels in the human cell line. The HCV-replicon assay was validated in parallel experiments using interferon-alpha-2b as a positive control. Cyclosporine was also tested by way of comparison. Compounds of the invention potently inhibit HCV replication in human liver cells to a greater extent than cyclosporin. In addition, when considering the level of cytotoxicity, many of the compounds of this invention exhibit a wider safety margin (for example, cytotoxicity $IC_{50}$ versus antiviral $EC_{50}$) than cyclosporine.

The results were as follows (unless otherwise stated all values are expressed in nM), "N/D" means that the data was not determined.

| Compound | HCV Activity | | Cytotoxicity | |
|---|---|---|---|---|
| | EC50 | EC90 | IC50 | IC90 |
| A | 60 | 220 | 2330 | >3000 |
| B | 1180 | 2720 | 6310 | 20310 |
| C | 180 | 640 | >3000 | >3000 |
| D | 290 | 1320 | 17200 | >20000 |
| E | 20001 | N/D | 15600 | N/D |
| F | 17000 | N/D | >20000 | N/D |
| G | <200 | 570 | 10300 | >20000 |
| H | <200 | 370 | >20000 | >20000 |
| I | 1010 | 1870 | 2830 | 17350 |
| J | 150 | 530 | 8201 | 19600 |
| K | 260 | 590 | 5500 | 17800 |
| L | 280 | 1250 | 11500 | >20000 |
| M | 3350 | 6111 | >20000 | >20000 |
| N | <200 | <200 | >20000 | >20000 |
| O | 122 | 300 | 13440 | >20000 |
| P | 230 | 580 | 6150 | >20000 |
| Q | 210 | 620 | 18880 | >20000 |
| R | 310 | 590 | 11100 | >20000 |
| S | 40 | 160 | >2000 | >2000 |
| T | 80 | 410 | >2000 | >2000 |
| U | 90 | 450 | >2000 | >2000 |
| V | 360 | 1200 | >2000 | >2000 |
| W | 130 | 510 | >2000 | >2000 |
| X | 480 | 1500 | >2000 | >2000 |
| Y | 300 | 950 | >2000 | >2000 |
| Salts of cpd O | | | | |
| phosphate | 130 | 470 | >2000 | >2000 |
| citrate | 110 | 410 | >2000 | >2000 |
| acetate | 100 | 300 | >2000 | >2000 |
| hydrochloride | 110 | 380 | >2000 | >2000 |
| MeSO2 | 160 | 500 | >2000 | >2000 |
| propionate | 100 | 320 | >2000 | >2000 |
| Cyclosporine | 400 | 1420 | 5780 | 19403 |

5.17 Example 22

Cyclophilin Binding and HCV Activity

The instant example provides further methods for evaluating the effectiveness of compounds of the invention for treating or preventing HCV infection in a subject in need thereof.

It has been demonstrated that certain cyclosporins are effective in treating or preventing HCV infection through the binding of the cyclosporin to cyclophilin B (CyPB). See Watashi et al., 2005, *Molecular Cell* 19:111–122; Nakagawa et al., 2005 *Gastroenterology* 129(3): 1031–41; the contents of which are hereby incorporated by reference in their entirety. Although not intending to be bound by any particular theory of operation, it is believed that cyclophilin B is critical for the efficient replication of the HCV genome. Cyclosporin A and derivatives of cyclosporin that inhibit cyclophilin B can dramatically reduce the replication of HCV in standard assays.

Accordingly, compounds of the present invention are shown to be effective for the treatment or prevention of HCV infection by evaluating their binding or modulation of cyclophilin, for instance cyclophilin B. Modulation of cyclophilin by a compound of this invention is measured according to standard techniques, for example, those described in Watashi et al., 2005, those described in Nakagawa et al., 2005, or those described in Billich et al., *J. Virol.* 69:2451–2461, the contents of which are hereby incorporated by reference in their entireties.

5.18 Example 23

HIV Activity

The compounds of the present invention were tested for antiretroviral activity against human immunodeficiency virus-1 (HIV) using infection of the human T-lymphoblastoid cell line, CEM-SS, with the HIV strain HIV-1IIIB (Weislow et al., 1989, *J. Natl. Cancer Inst.* 81:577–586). In this MTS cytoprotection assay, each experiment included cell control wells (cells only), virus control wells (cells plus virus), drug toxicity wells (cells plus drug only), drug colorimetric control wells (drug only) as well as experimental wells (drug plus cells plus virus). Compounds were first dissolved in DMSO and tested using six half-log dilutions, starting with a high concentration of either 20 or 2 µM. HIV-1RF was added to each well in a volume of 50 µL, the amount of virus determined to give approximately 90% cell killing at 6 days post-infection. At assay termination, assay plates were stained with the soluble tetrazolium-based dye MTS (CellTiter 96 Reagent, Promega) to determine cell viability and quantify compound toxicity. MTS is metabolized by the mitochondria enzymes of metabolically active cells to yield a soluble formazan product, providing a quantitative analysis of cell viability and compound cytotoxicity. The assay was validated in parallel experiments using Zidovudine (3'-azido-3'-deoxythymidine or AZT) as a positive control. The assay included determinations of compound $EC_{50}$ (concentration inhibiting virus replication by 50%), $IC_{50}$ (concentration resulting in 50% inhibition of cell growth) and a selectivity index ($IC_{50}/EC_{50}$).

The results for selected compounds were as follows (unless otherwise stated all values are expressed in nM).

| Compound | HIV Activity $EC_{50}$ | Cytotoxicity $IC_{50}$ | Selectivity Index $IC_{50}/EC_{50}$ |
|---|---|---|---|
| D | 1360 | >20000 | >15 |
| H | 1380 | 13300 | 10 |
| L | 1930 | 19500 | 10 |
| N | 350 | 20000 | 57 |
| O | 60 | 20000 | 333 |
| P | 160 | 6150 | 38 |
| Q | 230 | 18880 | 82 |

-continued

| Compound | HIV Activity $EC_{50}$ | Cytotoxicity $IC_{50}$ | Selectivity Index $IC_{50}/EC_{50}$ |
|---|---|---|---|
| R | 500 | 17300 | 35 |
| S | 90 | 14000 | 156 |
| T | 60 | 18000 | 300 |
| U | 110 | 13400 | 122 |
| V | 440 | >20000 | >45 |
| W | 680 | >20000 | >29 |
| X | 1000 | >20000 | >20 |
| Y | 520 | >20000 | >38 |

5.19 Example 24

Oral Dosage Forms

One or more of the compounds of the invention can be formulated as a capsule. Such a capsule can comprise 10 to 200 mg of the compound and on or more excipients selected from the group consisting of microcrystalline cellulose, pregelatinized starch, lactose, sodium starch glycolate, crospovidone, povidone, hydroxypropylcellulose, magnesium stearate and silicon dioxide. The resulting composition can be encapsulated with one or more standard encapsulation compositions such as gelatin or a plasticizer.

One or more of the compounds of the invention can be formulated as a salt in a syrup or elixir. The compound or compounds can be at a total concentration of 5 to 50 mg/mL. The syrup or elixir can further comprise polyethylene glycol, propylene glycol, mixtures of polyethylene glycol, PEG 400, a block copolymer of ethylene oxide and propylene oxide (e.g., poloxamer 407), polysorbate 20, ethanol, a sugar, citric acid and/or flavoring.

All publications and patent applications cited in this specification are herein incorporated by reference as if each individual publication or patent application were specifically and individually indicated to be incorporated by reference. While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating hepatitis C virus infection in a subject in need thereof, the method comprising administering to the subject a therapeutically effective amount of 3-[(R)-2-(N,N-dimethylamino)ethylthio-Sarcosine]-4-(gamma hydroxymethylleucine)cyclosporin of formula:

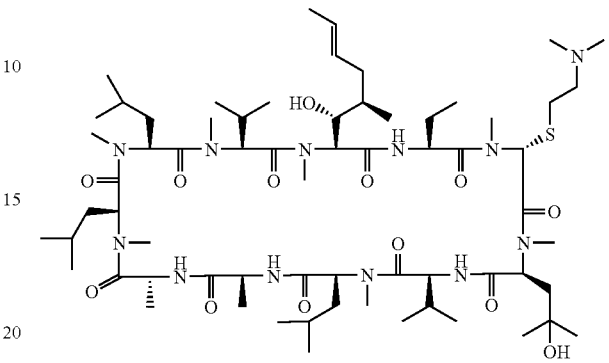

or a pharmaceutically acceptable salt thereof or a hydrate of said pharmaceutically acceptable salt.

2. The method according to claim 1 in which the 3-[(R)-2-(N,N-dimethylamino)ethylthio-Sarcosine]-4-(gamma hydroxymethylleucine)cyclosporin is administered orally.

3. The method according to claim 1, in which the amount of 3-[(R)-2-(N,N-dimethylamino)ethylthio-Sarcosine]-4-(gamma hydroxymethylleucine)cyclosporin administered is from about 1 to about 1000 mg per day.

4. The method according to claim 3, in which the amount of 3-[(R)-2-(N,N-dimethylamino)ethylthio-Sarcosine]-4-(gamma hydroxymethylleucine)cyclosporin administered is from about 50 to 500 mg per day.

5. The method according to claim 1 wherein said subject is refractory to treatment with interferon.

6. The method according to claim 1 wherein said subject is co-infected with HIV.

7. A method for treating hepatitis C virus infection in a subject infected with hepatitis C virus, the method comprising administering to the subject a therapeutically effective amount of 3-[(R)-2-(N,N-dimethylamino)ethylthio-Sarcosine]-4-(gamma-hydroxymethylleucine)cyclosporin of formula:

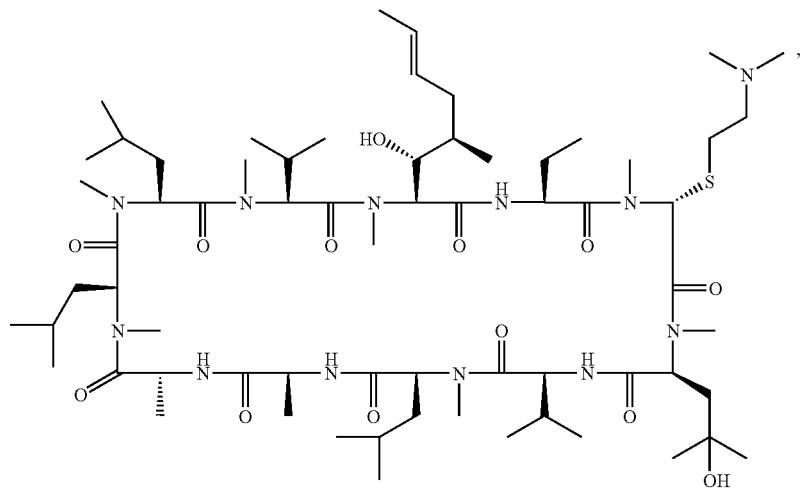

or a pharmaceutically acceptable salt thereof or a hydrate of said pharmaceutically acceptable salt.

8. The method of claim 1, wherein the pharmaceutically acceptable salt is a phosphate, citrate, acetate, chloride, methanesulfonate or propionate salt.

9. The method of claim 1 comprising administering a hydrate of the pharmaceutically acceptable salt.

10. The method of claim 7, wherein the pharmaceutically acceptable salt is a phosphate, citrate, acetate, chloride, methanesulfonate or propionate salt.

11. The method of claim 7 comprising administering a hydrate of the pharmaceutically acceptable salt.

* * * * *